US007735362B2

(12) United States Patent
DeNatale et al.

(10) Patent No.: US 7,735,362 B2
(45) Date of Patent: Jun. 15, 2010

(54) THERMOMECHANICAL SENSOR FOR FLUID DIAGNOSTICS

(75) Inventors: Jeffrey F. DeNatale, Thousand Oaks, CA (US); Robert L. Borwick, III, Thousand Oaks, CA (US); Philip A. Stupar, Oxnard, CA (US); Martin W. Kendig, Thousand Oaks, CA (US)

(73) Assignee: Teledyne Licensing, LLC, Thousand Oaks, CA (US)

( * ) Notice: Subject to any disclaimer, the term of this patent is extended or adjusted under 35 U.S.C. 154(b) by 500 days.

(21) Appl. No.: 11/395,022

(22) Filed: Mar. 31, 2006

(65) Prior Publication Data

US 2007/0231911 A1    Oct. 4, 2007

(51) Int. Cl.
*G01N 33/30* (2006.01)
(52) U.S. Cl. .............................. 73/114.55; 73/9; 73/10; 73/53.05; 73/54.42; 73/54.43; 73/114.56; 436/60
(58) Field of Classification Search ........................ 73/9, 73/10, 53.01, 53.02, 53.05, 54.42, 54.43, 73/114.55–114.56; 436/60
See application file for complete search history.

(56) References Cited

U.S. PATENT DOCUMENTS

| | | | |
|---|---|---|---|
| 5,955,659 A | 9/1999 | Gupta et al. | ............... 73/54.01 |
| 6,023,961 A | 2/2000 | Discenzo et al. | ........... 73/54.01 |
| 6,269,685 B1 | 8/2001 | Oden | ....................... 73/54.23 |
| 6,286,363 B1 * | 9/2001 | Discenzo | ................... 73/53.01 |
| 6,311,549 B1 | 11/2001 | Thundat et al. | ............ 73/54.24 |
| 6,525,334 B1 * | 2/2003 | Brackett | ...................... 250/573 |
| 6,647,778 B2 | 11/2003 | Sparks | ..................... 73/204.26 |
| 2002/0178780 A1 * | 12/2002 | Van Mullekom et al. | ....... 73/10 |
| 2003/0101801 A1 * | 6/2003 | Wilson et al. | .............. 73/54.01 |
| 2004/0025573 A1 * | 2/2004 | Jakoby | ...................... 73/54.42 |
| 2005/0039521 A1 * | 2/2005 | Han et al. | .................. 73/53.05 |
| 2005/0066711 A1 * | 3/2005 | Discenzo | ................... 73/64.56 |
| 2006/0010964 A1 * | 1/2006 | Sparks et al. | .............. 73/54.01 |

FOREIGN PATENT DOCUMENTS

EP           1519190 A2 *   3/2005

OTHER PUBLICATIONS

B. Jakoby, et al., Monitoring macro- and microemulsions using physical chemosensors, Sensors and Actuators A, pp. 209-214, vol. 115 (2004).
B. Jakoby, et al., Physical sensors for water-in-oil emulsions, Sensors and Actuators A, pp. 28-32, vol. 110 (2004).
Barnes, Viscosity—How It's Measured and Reported, Practicing Oil Analysis Magazine (Nov. 2002).
Durdag, Measuring Viscosity with a Surface Acoustic Wave Sensor, Sensors, pp. 34-36, vol. 22., No. 10 (Oct. 2005).
Durdag, Solid-State Viscometer for Oil Condition Monitoring, Practicing Oil Analysis Magazine (Nov. 2004).
ViSmart Overview Sheet, Biode, Inc., www.biode.com, 100 Larrabee Road, Westbrook, Maine 04092, 2003.

* cited by examiner

*Primary Examiner*—Jill Warden
*Assistant Examiner*—Shogo Sasaki
(74) *Attorney, Agent, or Firm*—Koppel, Patrick, Heybl & Dawson

(57) ABSTRACT

A method for diagnosing a fluid includes sensing a property of the fluid and the temperature of the fluid at the time the property is sensed, then determining the status of the fluid from the sensing. The sample volume may be small in comparison to the total fluid volume.

9 Claims, 4 Drawing Sheets

US 7,735,362 B2

THERMOMECHANICAL SENSOR FOR FLUID DIAGNOSTICS

BACKGROUND OF THE INVENTION

This invention is concerned with determining the condition of a fluid. A wide variety of fluids, such as lubricants, coolants, fuels, hydraulic fluids, paints and coatings, are used in many different types of machines and processes, such as aircraft, ground vehicles, ships, pumps, and manufacturing. The properties of such fluids can have a significant effect on the performance of the machine or process in which the fluid is utilized. Degradation of a fluid property can cause the system to operate at less than optimum efficiency or can even cause catastrophic failure and unscheduled downtime. Degradation of the mechanical and chemical properties of a lubricating fluid, for example, and the cleanliness of the lubricant, are all well known factors in degrading the performance of the machine being lubricated.

Consequently, the ability to accurately characterize such fluid properties can increase the efficiency of the machine or process involved. The increased efficiency can result not only in helping to extend the useful life of the machine and avoiding catastrophic failures from using degraded lubricants, but also in reducing cost through employing a lubricant for substantially all of its useful life, rather than discarding it prematurely. A common maintenance approach, for example, is to estimate the useful life of the lubricant and establish a fixed replacement interval for the lubricant based on the estimate. This practice, however, typically results in replacement of lubricants that have substantial remaining useful life. By contrast, the approach can also occasionally result in considerable damage to a machine or system when a lubricant experiences an unusually short lifetime and degrades before the fixed replacement interval has been reached.

For these reasons, it is desirable to be able to determine the current health and condition of a fluid and to also have the capability to predict the remaining useful life of a fluid.

A variety of techniques are known in the art for monitoring the properties of fluids. Some of these techniques, however, require observations to be made over a relatively long period of time in order to establish a trend in the fluid properties. Other techniques are too qualitative to produce data that can accurately characterize the fluid properties. In addition, some of these approaches, such as extracting a sample from the fluid and transporting the sample to a remote location for chemical analysis, are excessively time consuming and expensive.

Therefore, a need has developed in the art for a fluid diagnostic technique which can be performed locally on a small sample of the fluid, and which imposes minimal or no interference with the operation of the associated machine or process. Moreover, it would be advantageous to provide such a technique capable of fully evaluating the fluid to the point of failure.

BRIEF SUMMARY OF THE INVENTION

A method for diagnosing a fluid includes heating the fluid using a pseudo-adiabatic thermal stimulation through a predetermined temperature range at which a contaminant content is known to change a measured property of the fluid in comparison to the property in contaminant-free fluid through such pre-determined temperature range, sensing, a plurality of times, a property of the fluid and the temperature of the fluid at the time said property is sensed, and determining the status of the fluid from said sensing.

An advantage to the method involves measuring a property of a sample whose volume is small in comparison to the total fluid volume. One property that is especially useful is the viscosity of the sample.

The method can be used not only to establish the current health of the fluid, but also to predict the remaining useful life of the fluid. This can be accomplished in a number of ways, including comparing the sensed property values to theoretically predicted values of the property, as well as comparing the sensed property values to empirically measured values of the property.

In some applications, it will be advantageous to make a number of property measurements all at the same sample temperature, while in other situations it may be desirable to make the property measurements over a range of sample temperatures.

Particular embodiments of the invention include detecting the presence of a contaminant, including, for example, water or fuel in a lubricant.

A device for diagnosing a fluid includes, in accordance with the invention, a sensor for sensing a property of the fluid, a sensor for sensing the temperature of the fluid at the time the property is sensed, and an element for controlling the temperature of the sample, such that the status of the fluid can be diagnosed from a plurality of the property and temperature sensings.

DETAILED DESCRIPTION OF THE INVENTION

Figure 1:
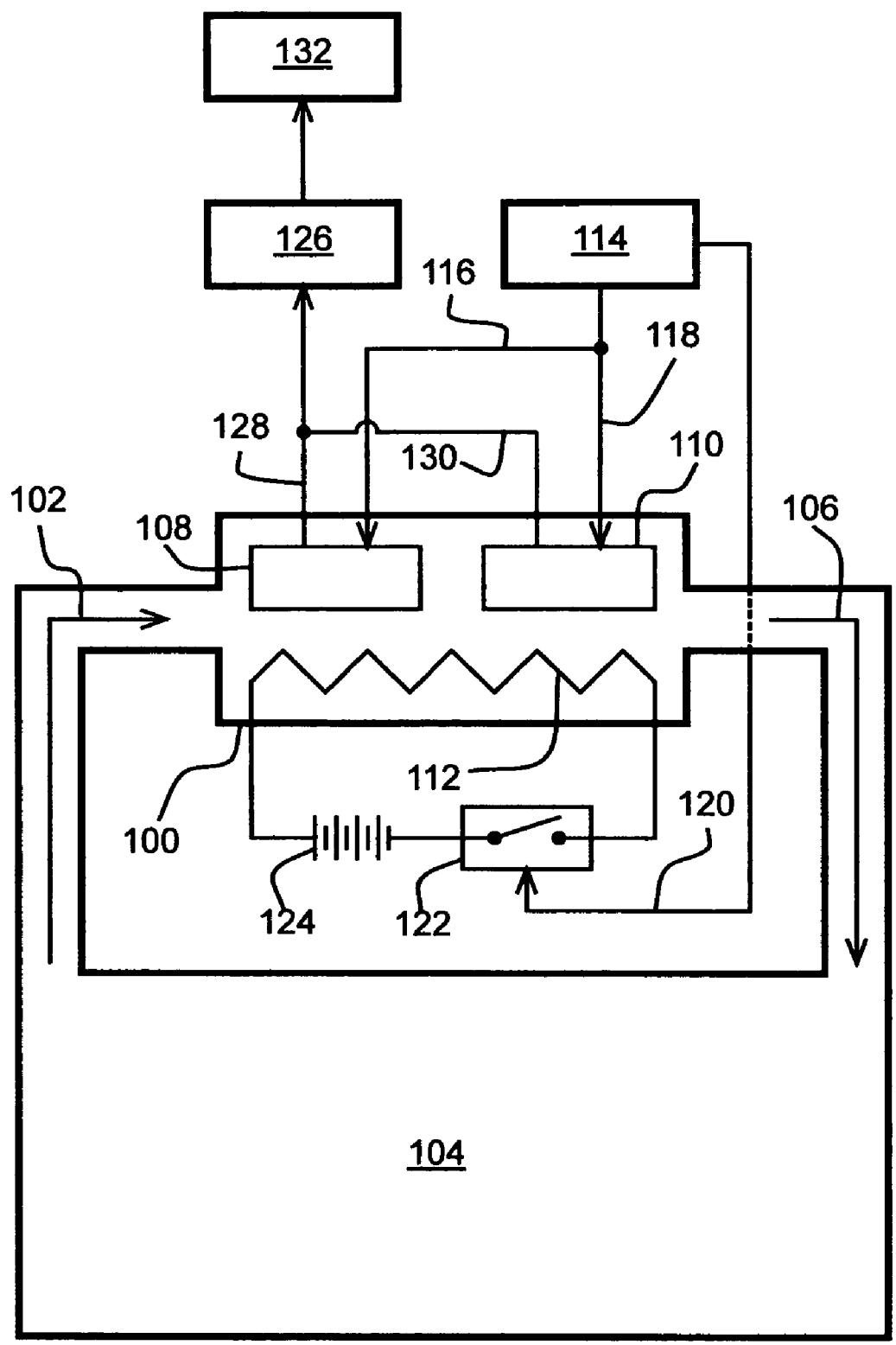
FIG. 1 is a schematic illustration of a device constructed according to the invention for diagnosing the status of a fluid.

In practicing the method of the invention, a property of a fluid is sensed and the temperature of the fluid at the time the property is sensed is also sensed. These steps are repeated a plurality of times, then the status of the fluid is determined, based on the property and temperature values obtained.

In one embodiment, a substantial advantage of the inventive method relates to the sample size. In this embodiment, the method is practiced with a sample size that is small in comparison to the total volume of the fluid that is being sampled, allowing the method to be carried out without substantially affecting the bulk of the fluid. Thus the method can be used on a fluid that is in service in its operating environment, such as, for example, the lubricating oil in an internal combustion engine.

Various embodiments of the inventive technique are expected to be useful for characterizing the status of a wide variety of fluids, such as, for example, lubricants, fuels, coolants, hydraulic fluids, paints, coatings, liquid food components in the food process industry, and fluids in the chemical process industry.

A variety of properties of a fluid can be useful in providing information about the status of the fluid. In more specific embodiments, the measured property is a mechanical property of the fluid, a chemical property (such as acidity, oxidation or water content), an electrochemical property, such as conductivity, pH, high frequency impedance or dielectric constant, or some measure of the fluid's cleanliness (particulate content, for example). One mechanical property of a lubricating fluid, its viscosity, is known to be particularly relevant in determining the condition of the fluid.

Embodiments of this invention are expected to be of particular utility not only in establishing the current health of a fluid, but also to predict the remaining useful life of the fluid. In addition, the diagnostic step may be performed, in more particular embodiments, by comparing the sensed property values to values for the corresponding sensed temperatures obtained via theoretical prediction techniques, or the values may be compared to known values obtained through empirical experimentation.

The manner in which the sensed property is related to temperature can be varied. For some diagnostic procedures, it may be desirable to repeat the sensing steps for a substantially constant sample temperature. This approach can be of value, for example, where the temperature of the sample is one at which the fluid is known to deteriorate, and the sensing steps are repeated over a sufficient period of time to observe enough deterioration of the fluid that information about the condition of the fluid is deductible from this data.

Alternatively, the sensing steps can be repeated for a number of different temperatures. Typically, this embodiment would be practiced, for example, by sensing the property over a period of time while the sample temperature is increased to a temperature at which the fluid properties experience a change. The initial and final temperatures at which water desorbs from a lubricating fluid, for example, reflect chemical binding properties that affect the condition of the fluid.

In particular, one known factor in the deterioration of fluids such as lubricants is the presence of a contaminant in the fluid. A useful embodiment of the inventive technique is to repeat the sensing steps over a range of sample temperatures that includes a temperature at which the contaminant content is known to change the measured property of the fluid. Two contaminants commonly affecting the health of a lubricant are water and fuel, and the invention can be employed to characterize the presence of those contaminants in a lubricating fluid.

By design, lubricating fluids, hydraulic fluids and fuels react slowly in the liquid state and generally have little or no ionic conductivity. The lack of ionic species in such fluids makes them slow to react to electrochemical probes or other measurements of chemical kinetics. Nevertheless, it is the relative reactivity of such fluids that determines their remaining useful life, which in turn relates to the ability to mitigate the degradation of mechanical or fluidic machine components. By using rapid, localized, pseudo-adiabatic thermal stimulation of a fluid, proximate to sensing elements that can rapidly assess transient degradation ("pseudo-adiabatic" meaning sufficiently rapid and localized thermal stimulation of a fluid slug of interest such that the fluid slug is deemed essentially free of heat transfer to its operating environment between the time of thermal stimulation and time of sensing by the sensing elements), the present invention makes possible the operation of electrochemical and other sensors within the ambient pressures and temperatures of such operational environments, while providing a sensitive measurement of chemical reactivity and other indicators of the fluid status.

Introduction of a controlled amount of heat for a controlled amount of time produces localized heating. The response of the fluid to this thermal transient enables the prediction of the remaining useful life of the fluid. A contaminant-free fluid will show a well defined rise in temperature, decrease in viscosity, and increase in conductivity that will return to original levels after the heat is turned off.

A contaminated fluid may show an initial drop in viscosity, followed by an irreversible rise, non-steady temperature variations, and conductivity transients as water is driven out of the sample. These characteristic behaviors can indicate reduced remaining life, and can also provide the reasons for the reduced life. In effect, this invention provides a micro accelerated testing laboratory.

FIG. 1 is a schematic illustration of a device, constructed according to one embodiment of the claimed invention, which can be used to diagnose a fluid. A container 100 is provided, into which a sample of the fluid can enter, as depicted by the arrow 102, from a larger volume of the fluid 104. An exit path for the sample is also provided, as indicated by the arrow 106, for return to the larger volume of fluid.

A property sensor 108 senses a property of the fluid sample, the property being characteristic of a condition of the fluid. Typically, when practicing this embodiment of the invention, multiple measurements of the fluid property are made, and a temperature sensor 110 may be used to sense the temperature of the sample at the time each such measurement is made. In addition, it is necessary in some embodiments of the invention to control the temperature of the sample; therefore, a heater 112 is positioned in the container 100, to heat the entire sample for that purpose.

Also shown for this embodiment is control electronics 114, which is connected, as shown by the lines 116 and 118, to the sensors 108 and 110, respectively. The control electronics is also configured to control the heater 112, as shown by the line 120, which acts on a switch 122 to selectively apply the power source 124 to the heater. Those skilled in the art will appreciate that this arrangement can be used to effect a variety of heating profiles, such as, for example, ramping the temperature up in a continuous fashion or increasing the temperature in discrete steps.

Readout electronics 126 receives input from the sensors 108 and 110, as shown by lines 128 and 130, respectively. Diagnostic electronics 132 uses the data from the readout electronics to determine the status of the fluid.

As mentioned in the description of the inventive method, the sensor 108 may, in more specific embodiments, sense a mechanical property of the fluid (such as viscosity), a chemical property, an electrochemical property, or the cleanliness of the fluid. Furthermore, it will be desirable with some embodiments of the heater 112 to be capable of raising the temperature of the fluid sample to at least a temperature that is known to effect changes in the fluid status. Contaminants, such as fuel and water, for example, are known to have a degrading effect on the condition of a lubricating fluid, and it may be desirable for the heater 112 to heat the sample to a temperature that causes substantial changes in the manner in which such a contaminant exists within a lubricating fluid. The solubility, for example, of contaminants (such as water or fuel) is dependent on temperature. By monitoring the change in a fluid property that is influenced by this solubility as a function of temperature, one can extract a measure of contaminant content.

An especially advantageous embodiment of the inventive device uses a MEMS (microelectromechanical system) sensor for the property sensor 108, integrated with the heater 112 and the temperature sensor 110 on a common substrate. A MEMS viscosity sensor has been shown, for example, to provide a sensitive measure of the moisture content of a lubricant when heated to a temperature at which water is desorbed from the lubricant. The presence of water in a lubricating fluid is known to reduce the lubricating quality for the fluid and to promote corrosion of metallic components within the system.

The nature of such water-related characteristics can be measured to determine the extent and degree of incorporation of the water. Because of the small dimensions of such a MEMS integrated design, only a small fluid sample volume is needed, reducing the power requirements for the device and avoiding large scale degradation of the lubricant. These features allow the device to be used in situ for machine health monitoring. Such an integrated device, for example, is shown and described in Borwick, et al., Modules Integrating MEMS Devices with Pre-Processed Electronic Circuitry, and Methods for Fabricating Such Modules, U.S. Pat. No. 6,979,872 (Dec. 27, 2005) the teaching of which is hereby incorporated by reference.

The invention is expected to be useful in a wide variety of applications for in situ monitoring, such as motors, pumps, vehicular equipment, fixed wing aircraft, rotary aircraft, and shipboard equipment.

Figure 2:
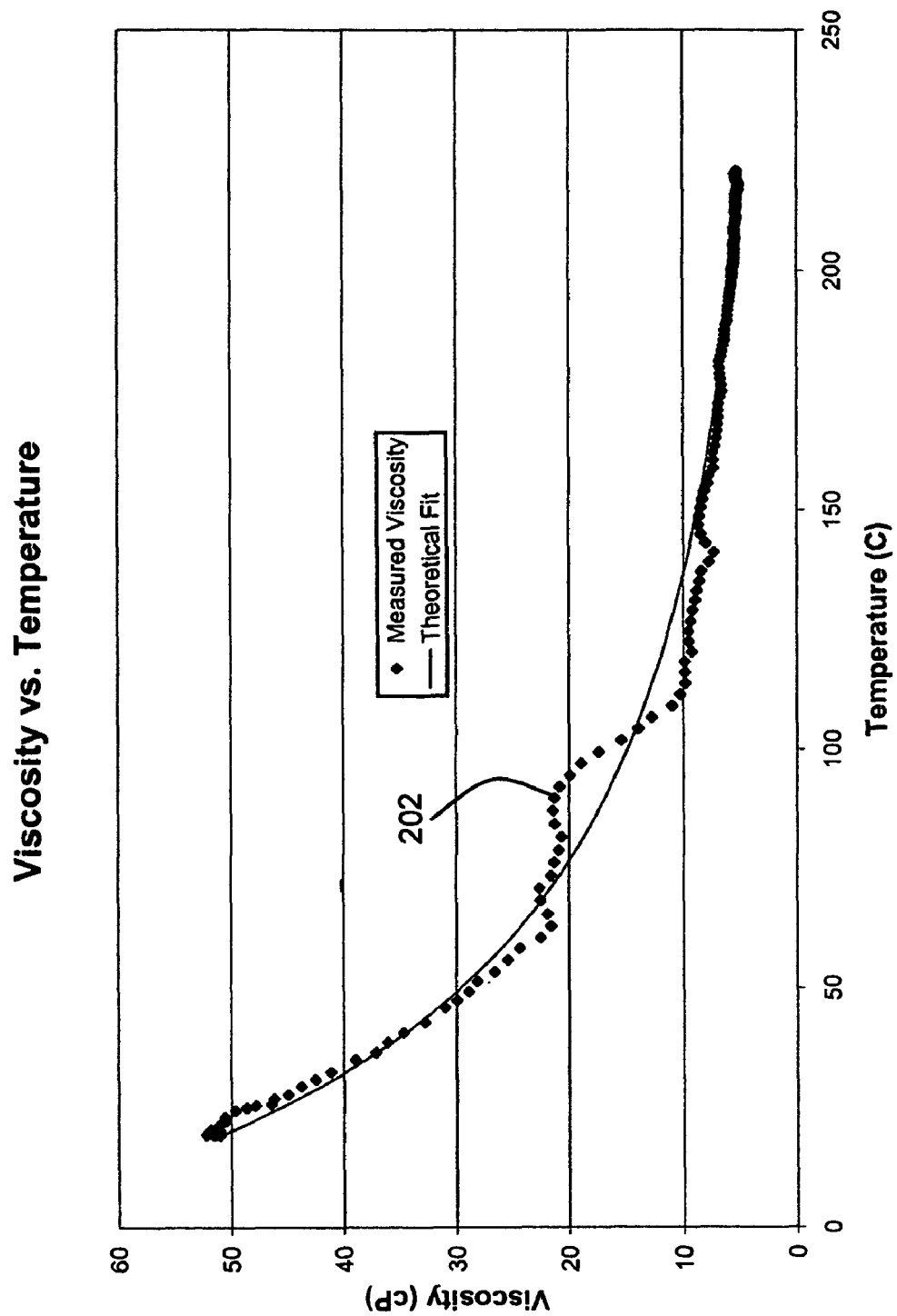
FIG. 2 is a plot of viscosity versus temperature representing experimental test results on a sample of lubricating fluid.

Testing of the inventive concept was accomplished by placing a device constructed according to one embodiment of the invention, including a MEMS viscosity sensor (for an example of a MEMS viscosity sensor, see, e.g., Sparks, Integrated Microtube Sensing Device, U.S. Pat. No. 6,647,778 (Nov. 18, 2003)), in 40 mL of Castrol® 5050 lubricating oil from Castrol Limited LTD Liab. Co. and heating the fluid to a maximum temperature of 224° C. FIG. 2 is a plot of the viscosity measurements obtained as a function of temperature. The theoretical viscosity as a function of temperature is also plotted in the figure, as calculated using the relationship Viscosity=$Ae^{(B/T)}$ where A and B are constants for the particular fluid, and T is temperature.

Figure 3:
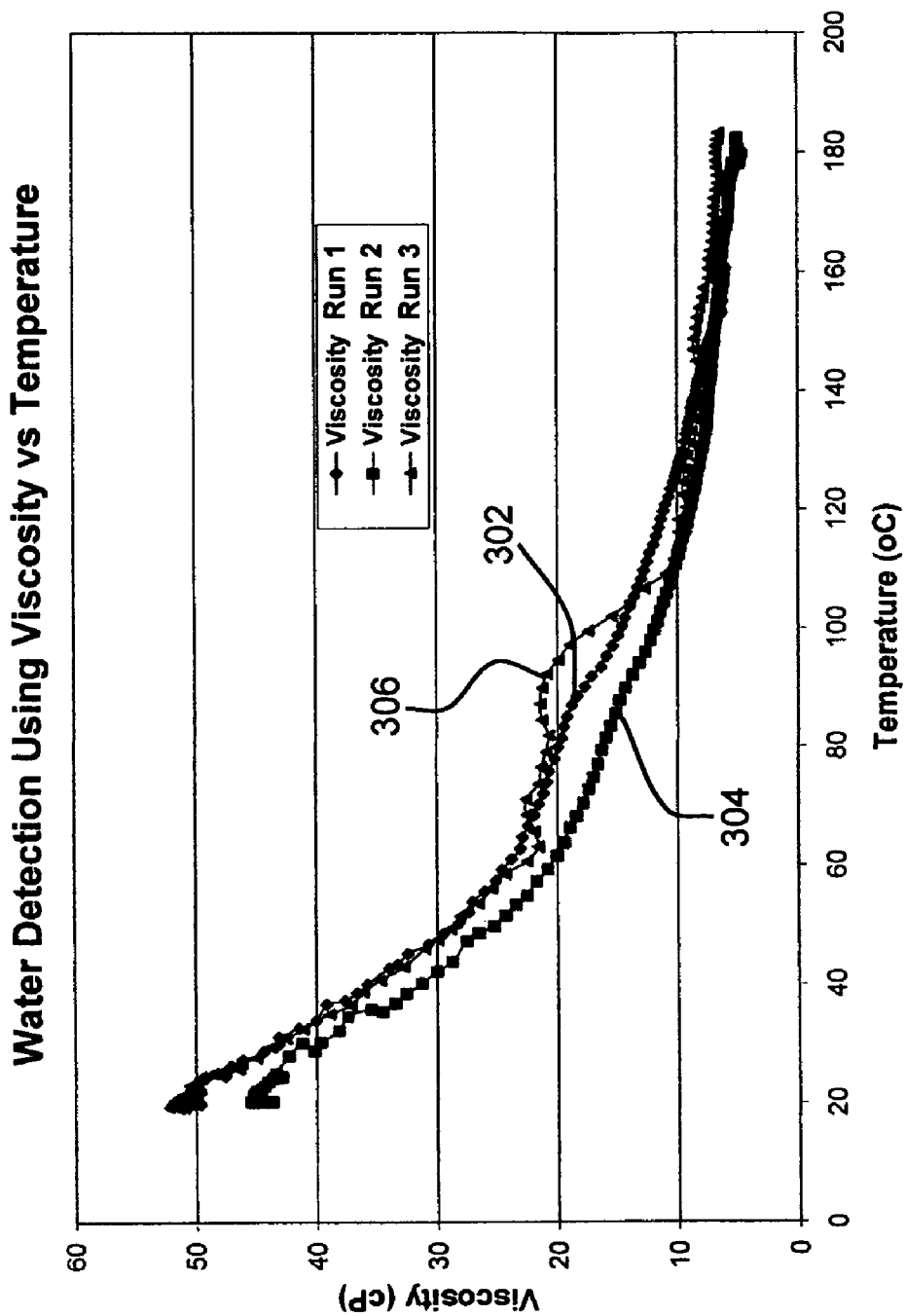
FIG. 3 is also a plot of viscosity versus temperature for test results on a sample of lubricating fluid, showing the efficacy of the invention for relating the water content of a lubricating fluid to the condition of the fluid.

This experiment demonstrated, as shown by an anomaly 202 in the measured results, that the method of this invention can be used to detect water in solution in the lubricating fluid. This methodology detects changes in a fluid property caused by water solubility, providing a means for determining the water content of the lubricant. FIG. 3 is a second plot of viscosity as a function of temperature, for the same type of Castrol® 5050 lubricant. This data was obtained by performing three runs of viscosity/temperature measurements using the same experimental setup as described with respect to FIG. 2. Run 1 was performed on a fresh sample of fluid. The small "hump" 302 in the Run 1 curve indicates that a small amount of water was present in the fluid. Run 2 was accomplished after allowing the lubricant sample to cool for one hour following Run 1. The smaller hump 304 displayed by the Run 2 data suggests that most of the water in the lubricant was driven out during the heating cycle of Run 1. Finally, Run 3 was performed on the lubricant sample after several hours of degradation and 14 hours of allowing the fluid to sit at 20° C. in ambient lab atmosphere. The larger hump 306 in the Run 3 data shows that water has redissolved into the fluid, reflecting increased fluid degradation.

Figure 4:
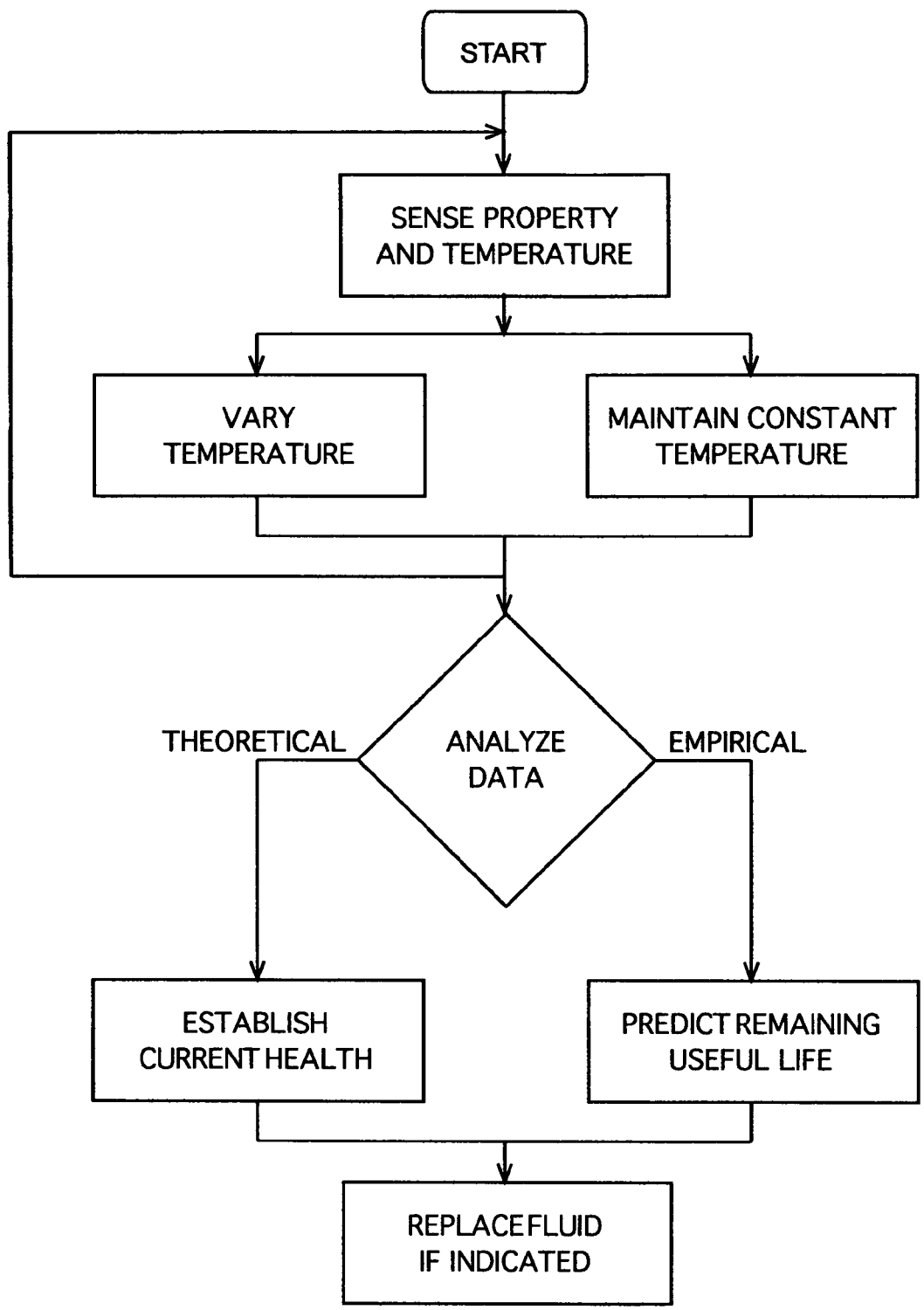
FIG. 4 is a flow chart depicting a method for diagnosing a fluid according to the present invention.

FIG. 4 is a flow chart that illustrates some of the embodiments in which the method of this invention may be practiced. A fluid is diagnosed by first sensing a property of the fluid and the temperature. The temperature of the fluid may be varied or may be maintained at a constant temperature, and the sensing step is repeated.

After a suitable number of repetitions of sensing, the data is analyzed. This analysis may involve comparing the sensed property values to theoretically predicted values or to empirically measured values.

Once the data is analyzed, the results may be used to establish the current health of the fluid or to predict the remaining useful life of the fluid. Finally, the appropriate action is taken, such as replacing the fluid if the diagnosis indicates replacement is advisable.

The preferred embodiments of this invention have been illustrated and described above. Modifications and additional embodiments, however, will undoubtedly be apparent to those skilled in the art. Although a single property sensor, for example, is disclosed in the embodiments described, it may be desirable to incorporate multiple sensors for more extensive fluid property measurements. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

The invention claimed is:

1. A method for diagnosing the health of a machine fluid by investigating an extent of degradation of the fluid due to contaminants in the fluid, comprising steps of:

selecting a contaminant of interest, which is known to change a measured property of the fluid;

detecting the presence of said contaminant in the fluid by:

(a) heating a sample of fluid using a pseudo-adiabatic thermal stimulation through a range of temperature at which said contaminant changes said measured property of the fluid in comparison to the property of contaminant-free fluid with respect to said range of temperature;

(b) sensing and measuring, a plurality of times, the property of the fluid through said range of temperature;

(c) storing the property measurements as a function of said range of temperature and comparing said function to a function of the property values of contaminant-free fluid over said range of temperature;

(d) identifying the anomaly in said range of temperature for detecting the presence of the contaminant;

cooling the sample of fluid;

repeating the detection steps (a)-(d);

comparing the anomaly identified in repeated detections; and determining the current health of the fluid.

2. The method of claim 1, wherein said measured property comprises viscosity.

3. The method of claim 1, wherein the step of determining the current health comprises predicting the remaining useful life of the fluid.

4. The method of claim 1, wherein the step of comparing said function comprises comparing said function to a function derived from theoretical values of the property against said range of temperature.

5. The method of claim 1, wherein the step of comparing said function comprises comparing said function to a function derived from empirically measured values of the property against said range of temperature.

6. The method of claim 1, wherein the step of sensing and measuring, a plurality of times, comprises repeating the sensing steps a plurality of times at a substantially constant fluid temperature.

7. The method of claim 1, further comprising, after the step of determining the current health, taking remedial action in accordance with the determined health.

8. The method of claim 1, wherein said heating step further comprises heating the sample of fluid in discrete temperature steps.

9. The method of claim 1, wherein the heating step further comprises ramping up the temperature in a continuous fashion.

* * * * *